(12) United States Patent
Keränen et al.

(10) Patent No.: US 10,687,943 B2
(45) Date of Patent: Jun. 23, 2020

(54) ANNULOPLASTY SYSTEM

(71) Applicant: Medtentia International Ltd Oy, Espoo (FI)

(72) Inventors: Olli Keränen, Bjärred (SE); Ger O'Carroll, Castlebaldwin (IE)

(*) Notice: Subject to any disclaimer, the term of this patent is extended or adjusted under 35 U.S.C. 154(b) by 228 days.

(21) Appl. No.: 15/323,421

(22) PCT Filed: Jul. 3, 2015

(86) PCT No.: PCT/EP2015/065203
§ 371 (c)(1),
(2) Date: Jan. 1, 2017

(87) PCT Pub. No.: WO2016/001407
PCT Pub. Date: Jan. 7, 2016

(65) Prior Publication Data
US 2017/0156862 A1    Jun. 8, 2017

(30) Foreign Application Priority Data
Jul. 3, 2014   (EP) .................................... 14175538

(51) Int. Cl.
*A61F 2/24*   (2006.01)

(52) U.S. Cl.
CPC .......... *A61F 2/2463* (2013.01); *A61F 2/2445* (2013.01); *A61F 2220/0008* (2013.01); *A61F 2220/0091* (2013.01)

(58) Field of Classification Search
None
See application file for complete search history.

(56) References Cited

U.S. PATENT DOCUMENTS

| | | | |
|---|---|---|---|
| 2002/0013571 A1 | 1/2002 | Goldfarb | |
| 2004/0127982 A1* | 7/2004 | Machold | A61F 2/2418 623/2.36 |
| 2013/0066341 A1 | 3/2013 | Ketai | |
| 2014/0163669 A1 | 6/2014 | Ben-Zvi | |

FOREIGN PATENT DOCUMENTS

| | | |
|---|---|---|
| JP | 2014506175 A | 10/2010 |
| WO | 2004030569 A2 | 4/2004 |
| WO | 2010115596 A1 | 10/2010 |
| WO | 2013106585 A1 | 7/2013 |

* cited by examiner

*Primary Examiner* — Leslie Lopez
(74) *Attorney, Agent, or Firm* — Patent Grove LLC; Tomas Friend

(57) ABSTRACT

An annuloplasty device for repairing a heart valve comprises a first and a second support member that overlap each other and form a scissor linkage. The first and second support members are configured to pinch leaflets of the heart valve.

16 Claims, 7 Drawing Sheets

ANNULOPLASTY SYSTEM

FIELD OF THE INVENTION

This invention pertains in general to the field of annuloplasty devices, and in particular to an annuloplasty device comprising at least two overlapped support members and a method therefore.

BACKGROUND OF THE INVENTION

In today's annuloplasty devices it is generally a main single member device which is inserted into the heart and which contacts the leaflets to hold and reshape them according to a desired treatment. The devices of today may comprise additional periphery components that help in various ways to contact, hold and reshape the leaflets. A problem with today's devices is that they are getting more and more complex due to advanced shapes, materials and so on for reshaping the leaflets. The complexity of these devices also means that the time to deploy such devices into a heart is long.

WO2013I065 discloses an endoluminal support structure being a medical stent that includes a plurality of longitudinal strut members interconnected by a plurality of swivel joints. However, such devices would have the drawback that they would need further attachment means for securing it to the leaflets and performing any type of annuloplasty and having a very structural complex design.

Hence, an improved annuloplasty device would be advantageous and in particular allowing for a less complex procedure, quicker deployment and a less complex device.

SUMMARY OF THE INVENTION

Accordingly, examples of the present disclosure preferably seek to mitigate, alleviate or eliminate one or more deficiencies, disadvantages or issues in the art, such as the above-identified, singly or in any combination, according to the appended patent claims.

According to a first aspect of the invention an annuloplasty device for repairing a heart valve is disclosed. The annuloplasty device comprises valve tissue including an annulus and a pair of leaflets, comprising an atrial side 16 and a ventricular side 17. The annuloplasty device also comprises a first and a second support member, and wherein the support members, overlap each other for forming a scissor linkage, and wherein the first and second support members are configured to pinch the leaflets.

According to a second aspect of the invention a method of arranging an annuloplasty device comprising first and a second support members at a heart valve having leaflets and commissures is disclosed. The method comprises providing access to the heart, arranging the first support member to extend between the commissures and through the heart valve, whereby a proximal end of the first support member is configured to contact the atrial side of a first leaflet and a distal end is configured to abut a ventricular side of a second leaflet, arranging the second support member to extend between the commissures and through the heart valve, whereby a proximal end of the first support member is configured to contact the atrial side of said second leaflet and a distal end is configured to abut a ventricular side of said second leaflet, and fixating the first and second support members to pinch the tissue of said heart valve.

Further examples of the disclosure are defined in the dependent claims, wherein features for the second and subsequent aspects of the invention are as for the first aspect mutatis mutandis.

Some examples of the disclosure provide for a scissor linkage with improved pinch effect.

Some examples of the disclosure provide for support members at the leaflets that both hold as well as reshape the leaflets.

Some examples of the disclosure provide for support members to be moved freely together or individually in any direction to ease deployment and/or pinching of the leaflets.

Some examples of the disclosure provide for support members to overlap in various ways such that a very flexible annuloplasty device is achieved.

Some examples of the disclosure provide for an annuloplasty device which are adaptable to different thicknesses of the leaflets.

Some examples of the disclosure provide for an annuloplasty device which are adaptable to different sizes of the leaflets.

Some examples of the disclosure provide for an annuloplasty device which are adaptable to different defects of the leaflets.

Some examples of the disclosure provide for an annuloplasty device which are capable of being used in various types of defects of a patient.

Some examples of the disclosure provide for an annuloplasty device which is easily collapsed and deliverable by a catheter.

Some examples of the disclosure provide for an annuloplasty device which is easily arranged at a desired position at the leaflets.

Some examples of the disclosure provide for an annuloplasty device being easily guided around chordae.

Some examples of the disclosure provide for support members being flexible.

Some examples of the disclosure provide for an annuloplasty device which is additionally secured to the heart.

Some examples of the disclosure provide for an annuloplasty device having increased pinch effect between the two supports.

Some examples of the disclosure provide for an annuloplasty device which is pre-tensioned for increased pinch effect.

Some examples of the disclosure provide for an annuloplasty device comprising depressions for forming a pivot point of the scissor linkage for increased pinch effect.

Some examples of the disclosure provide for an annuloplasty device comprising a through hole on one support member and an extended pin or the like on the other support member for forming a pivot point of the scissor linkage for increased pinch effect.

Some examples of the disclosure provide for an annuloplasty device which is customisable to a patient and/or a delivery device and/or a defect.

Some examples of the disclosure provide for an annuloplasty device which is overall compact.

Some examples of the disclosure provide for an annuloplasty device which is easily maneuverable in the catheter and in the heart.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF EMBODIMENTS

Figure 1A:
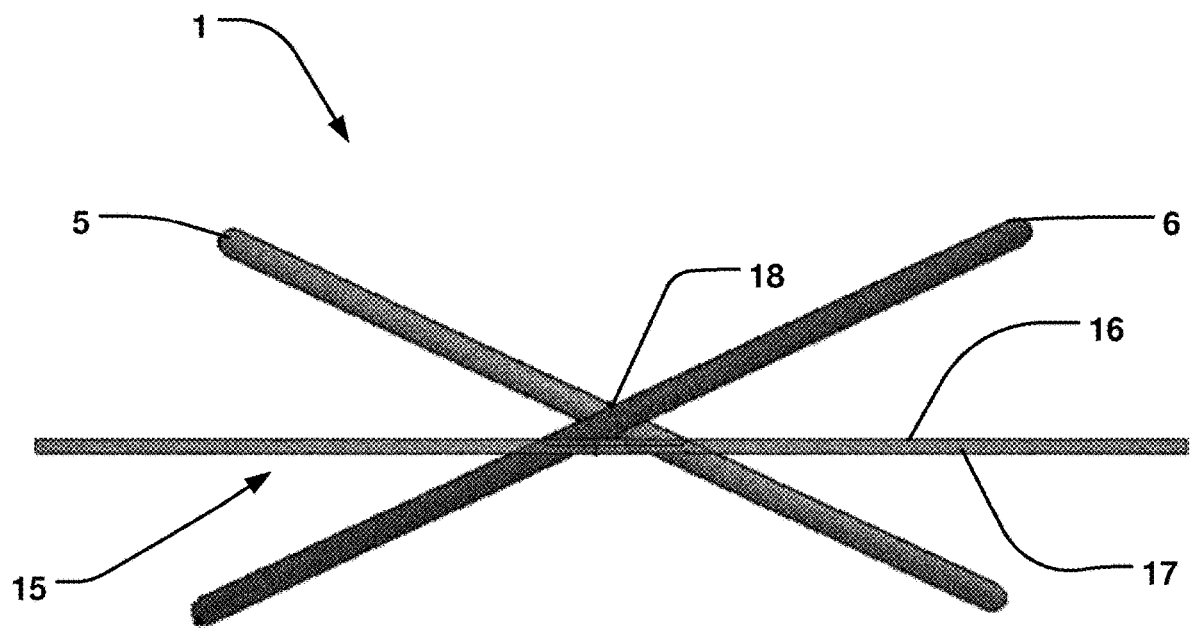
FIGS. 1a-b are cross sectional views of an annuloplasty device arranged at a leaflet according to an example of the invention.

Specific examples of the disclosure will now be described with reference to the accompanying drawings. This invention may, however, be embodied in many different forms and should not be construed as limited to the examples set forth herein. Rather, these examples are provided so that this disclosure will be thorough and complete, and will fully convey the scope of the invention to those skilled in the art. The terminology used in the detailed description of the examples illustrated in the accompanying drawings is not intended to be limiting of the invention. In the drawings, like numbers refer to like elements.

Figure 1B:
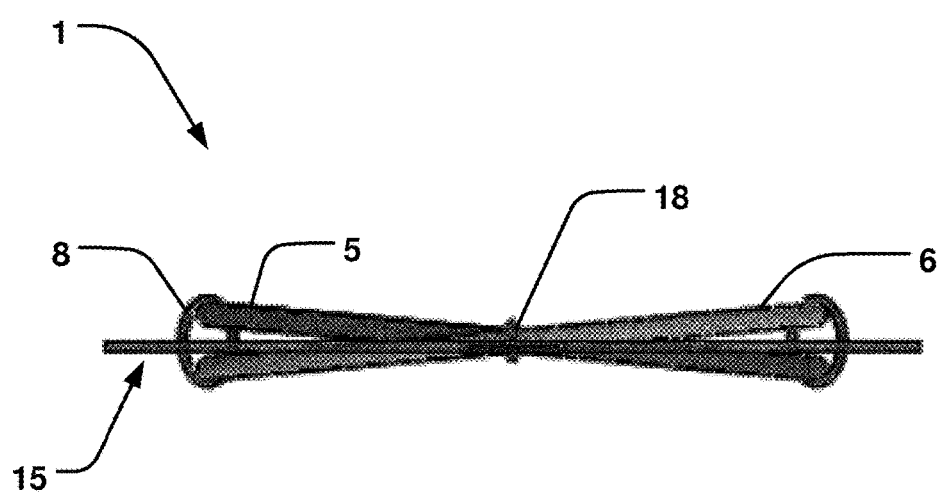

FIGS. 1a-b illustrate an example of an annuloplasty device 1 for repairing a heart valve. The heart valve comprises valve tissue including an annulus and a pair of leaflets 15 having an atrial side 16 and a ventricular side 17. The annuloplasty device 1 comprises a first 5 and a second 6 support member, and wherein the support members 5, 6 overlap each other for forming a scissor linkage 18. As illustrated in e.g. FIG. 4, the scissor linkage 18 is configured to provide a scissor—or clamping effect between the first and second supports 5, 6, that will fixate the annuloplasty device 1 at the heart valve. Thus the tissue is clamped or wedged in the scissor linkage 18, and further between the first and second support members extending around the annulus. By having the first 5 and second 6 members on the atrial 16 and ventricular 17 side of the pair of leaflets 15 and being overlapped forming a type of a scissor linkage there will thus be a resulting pinch effect between the support members 5, 6 at their ends, which will retain the support members 5, 6 at the leaflets 15 as well as reshape the leaflets. The first 5 and second 6 support members are arranged with one proximal end at the atrial side 16 and the opposite distal end at a ventricular side 17, in an alternated configuration. This is achieved by arranging them through the commissures 12, 13, and the valve and by overlapping the first and second support members 5, 6, as illustrated in FIGS. 2 and 4-6. This provides for a particularly easy fixation of the device 1 at the heart valve, e.g. very few sutures, clips or fastening elements 8 will be required as described further below with reference to FIGS. 5-6, while maintaining a secure fixation, and thereby an enhanced annuloplasty procedure.

In other words, the annuloplasty device 1 comprises a first support member having a proximal and a distal end. The proximal end of the first support member 5 is configured to contact the atrial side 16 of a first leaflet of a pair of leaflets of the valve, and the distal end is configured to abut the ventricular side 17 of a second leaflet of the pair of leaflets. The annuloplasty device also comprises a second support member 6 having a proximal and a distal end, the proximal end of the second support member is configured to abut the atrial side 16 of said second leaflet of the pair of leaflets, and the distal end is configured to abut the ventricular side 17 of said first leaflet of the pair of leaflets. The first and second support members are overlapped for forming a scissor linkage 18 at the commissures of the heart valve, as illustrated in e.g. FIG. 4.

Figure 2:
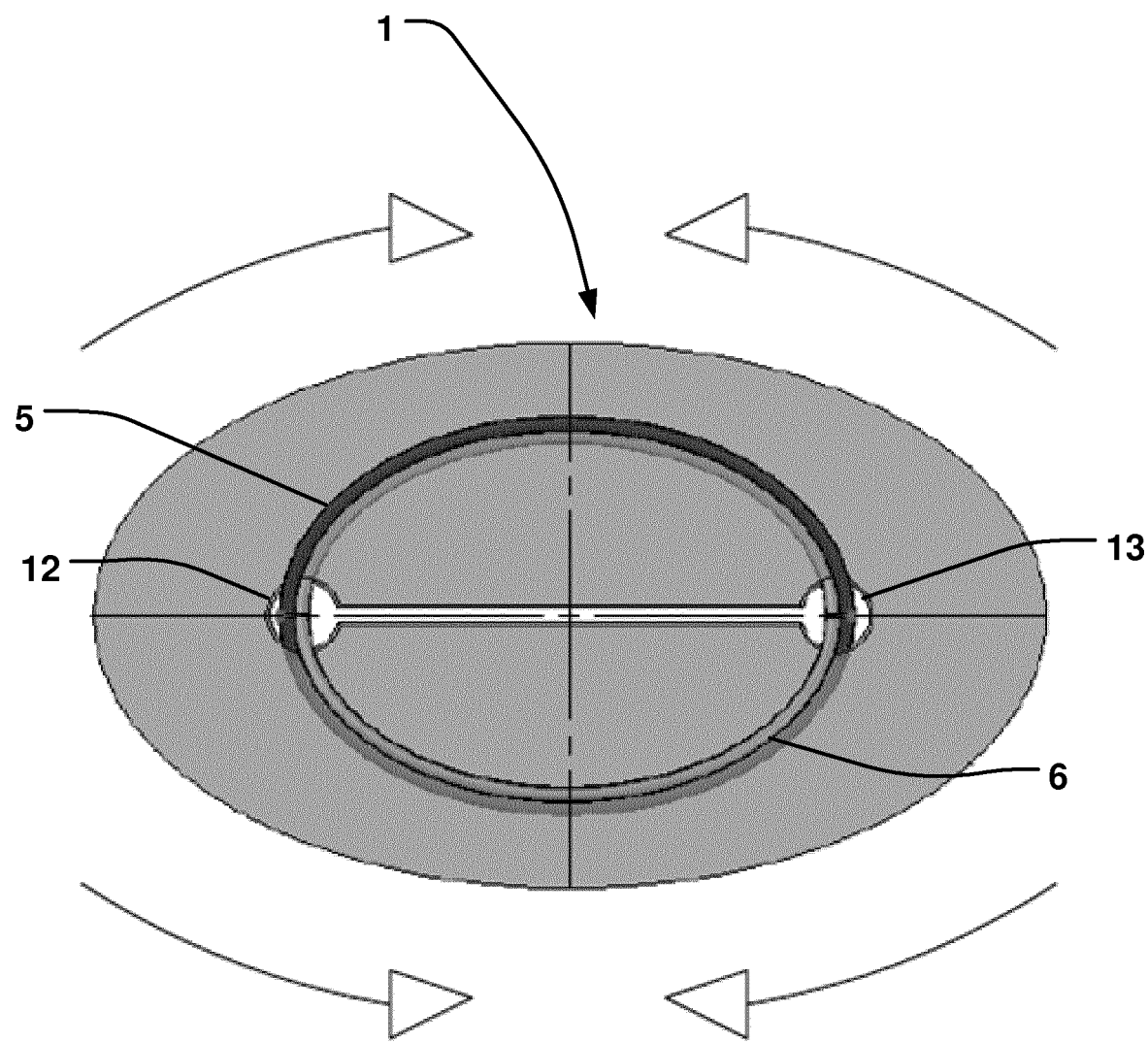
FIG. 2 is a top view of an annuloplasty device arranged in a heart according to an example of the invention.

In an example the support members 5, 6, are loosely overlapped and/or pre-assembled and can be moved freely together or individually in any direction to ease deployment and/or pinching of the leaflets 15, as illustrated by the arrows in FIG. 2.

In an example, illustrated in FIGS. 1-6, the first support member 5 and second support member 6 are substantially parallel symmetric, i.e. the two supports 5, 6 cross each other at their centre or half their respective lengths. This may provide for a particularly secure fixation of the annuloplasty device 1.

In another example the first support member 5 and second support member 6 are parallel asymmetric, i.e. the first support member 5 is off-centre relative to the second support member 6, or vice versa. By configuring the two support members 5, 6 to overlap in various ways, a very flexible annuloplasty device 1 is achieved and which is adaptable to different thicknesses, sizes, defects and so on of the leaflets 15, thus being usable in various types of defects of a patient.

In an example, illustrated in FIG. 2, the first support member 5 overlaps entirely the second support member 6. By having the first support member 5 substantially entirely overlapping the second support member 6, the annuloplasty device 1 is easily collapsed and deliverable by a catheter. By substantially overlapping is meant that one of the support members 5 is substantially encompassed by the other support member 6, when in a same plane. The annuloplasty device 1 may be collapsed by rotating the first 5 and second 6 support member relative to each other, or by completely separating the two support members 5, 6 and deliver them separately through the catheter.

The support members 5, 6, may be formed of a shape-memory material to have a relaxed expanded shape, and a compressed shape of reduced cross-section for delivery through a catheter. The support members 5, 6, may be connected in the compressed shape, or be separated in the compressed shape, when delivered through the catheter. When delivered in the connected configuration, the support members may be delivered in a single rotational motion as described. Having the support members separated during delivery may allow insertion of more rigid support members through the catheter, or insertion of support members each having a larger cross-section in the compressed shape. Thus the two-part configuration of the annuloplasty device provides for more flexibility in the choice of support characteristics to fit a particular anatomy, or desired mechanical properties of the supports.

The first 5 and second 6 support members are in some examples formed as substantially elongated or circular shaped continuous members. In some examples, the first 5 and second 6 support members comprises an opening for guiding around the chordae of the valve, at an end of the first 5 and second 6 support members, e.g. at any section along the periphery thereof. By having the opening at the end of the support members, they are easily arranged at a desired position at the leaflets 15 and the annulus. This easy arrangement is due to the support members 5, 6 being capable of being guided around the chordae by use of the opening. In an example the support members 5, 6 are flexed outwards from their relaxed state, allowing the opening to be wider and to be guided around chordae. In another example the opening is large enough without the support members 5, 6 being flexed outwards so that the support member 5, 6 are easily threaded, rotated or guided around the chordae, anyway.

In an example the first 5 and second 6 support members are configured for encompassing substantially all chordae. By encompassing almost all, or all of the chordaes, the device 1 is additionally secured to the desired position at the valve, and the support members 5, 6 are at a desired position, in contact with the leaflets 15 both from an atrial side and a ventricle side, and close to the heart wall. In other examples the support members 5, 6 are arranged close to, and/or encompassed by, the chordae, further away from the heart wall, closer to the centre of the valve, in contact with the leaflets 15 from both the atrial side and the ventricle side.

Figure 3A:
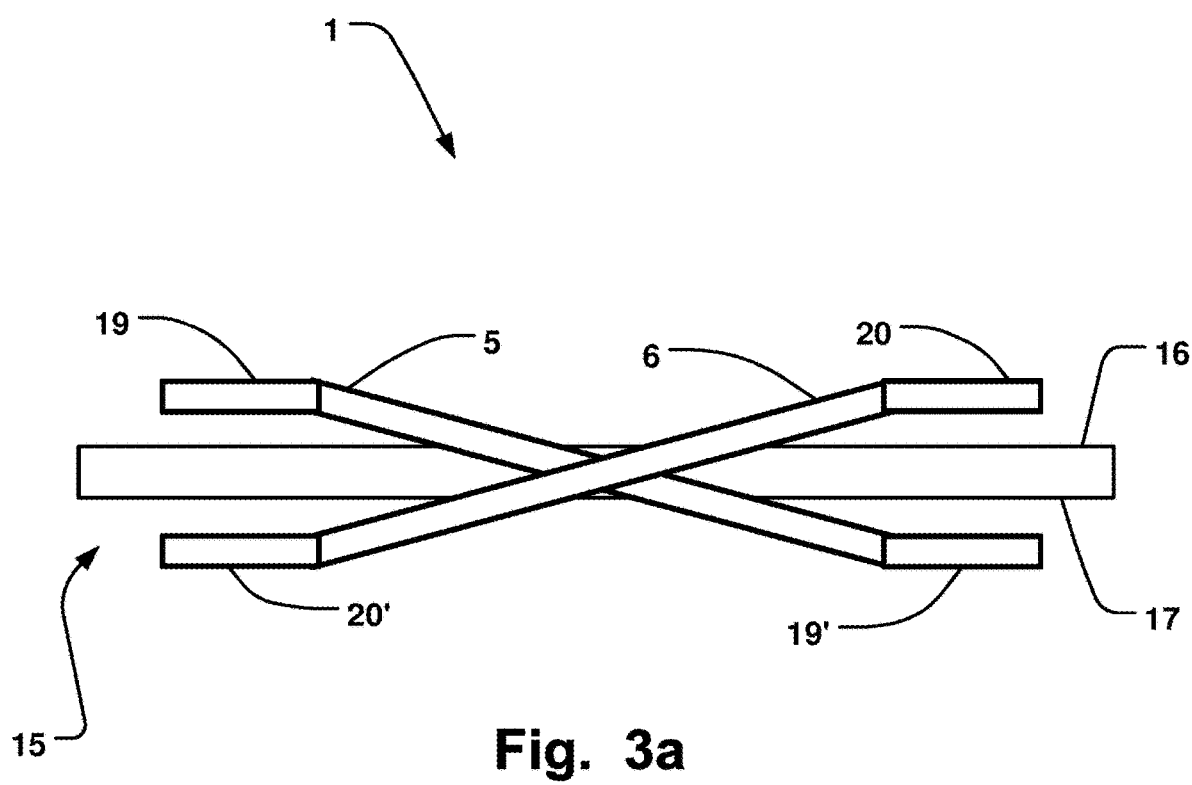
FIGS. 3a-b are cross sectional views of an annuloplasty device at a leaflet according to an example of the invention.
Figure 3B:
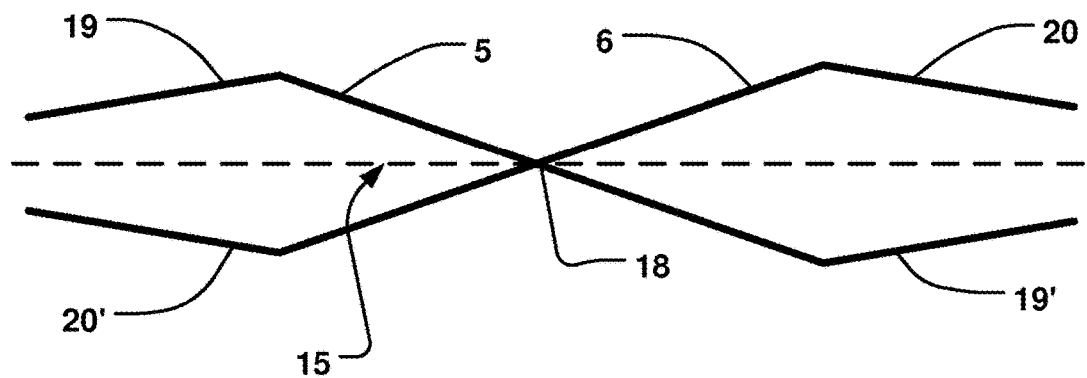

In another example the first support member 5 and/or second support member 6 are angulated. By angling the support members 5, 6 there will be an increased pinch effect between the two supports. The support members 5, 6 are in some examples angled towards each other at an end of the support members 5, 6, as can be seen in FIGS. 3a-b. I.e. the first support member 5 and/or second support member 6 may comprise angled portions 19, 19', and 20, 20', respectively, at opposite ends thereof. Further, as connection elements 7 of the scissor linkage 18 may be configured to fixate the first and second supports 5, 6, at a fixed angle relative each other, by a locking member, as described further below, the angled portions 19, 19', 20, 20', may press against the valve tissue when having an angle towards the tissue, as emphasized in FIG. 3b. This may further improve fixation of the annuloplasty device 1 at the valve.

In other examples only one of the support members 5, 6 is angled towards the other support member 5, 6. In some examples, the first 5 and second 6 support members are angled on one side only, thus pinching one leaflet 15 more, or less, than the other side pinching the other leaflet 15. In an example the first 5 and second 6 support members may be pre-tensioned, and when delivered at their desired location inside the heart, the pre-tension is released and the first 5 and second 6 support members are urged to their relaxed states. The relaxed state is configured so that the first 5 and second 6 support members are pinching and re-shaping the leaflets 15.

Figure 4:
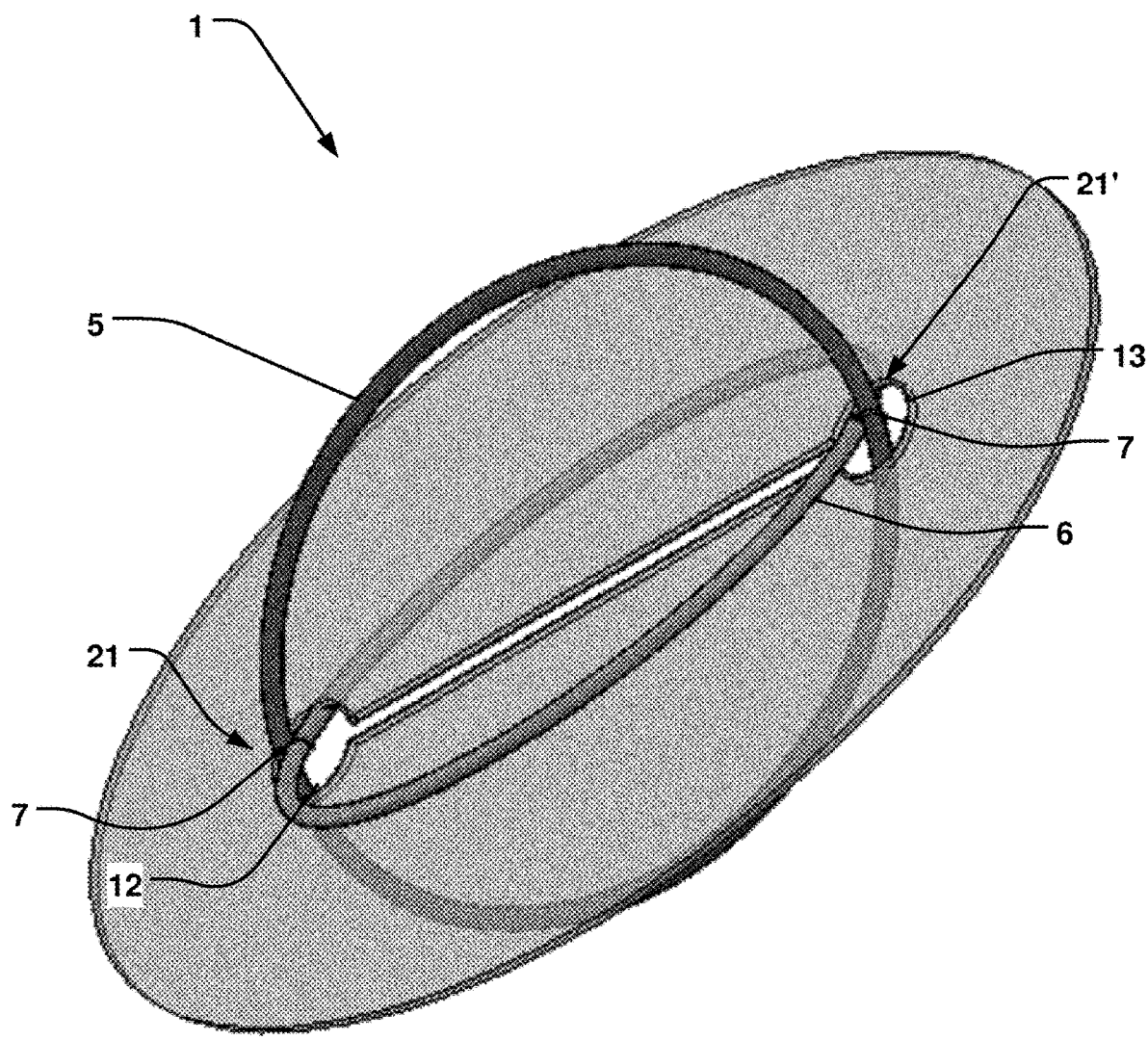
FIG. 4 is side view of an annuloplasty device arranged in a heart according to an example of the invention.

The scissor linkage 18 may comprise at least one connection element 7 arranged at the periphery of said first and second support members 5, 6, i.e. at a peripheral point of the support members to be arranged at the commissures 12, 13, of the valve, as illustrated in e.g. FIG. 4. The first and second support members may thus be connected at said at least one connection element 7. The connection element will exert a counter force on the first and second supports 5, 6, when pinching the tissue therebetween, as seen in e.g. FIG. 1b. In some examples, the scissor linkage comprises two radially opposed connection elements 7 at the respective commissures as seen in e.g. FIG. 4.

The at least one connection element 7 may comprise a hinge or pivot joint 21, 21'. The first and second support members are thus rotatable relative each other and in opposite directions. The clamping or pinching force between the first and second supports can thus be regulated by varying the angle therebetween, so that the supports can be fitted in a large variety of anatomical situations, and procedures. The hinges or pivot joints 21, 21', may be arranged at opposite peripheries of each of said first and second support members.

The first and second support members 5, 6, may be releasably connected at the at least one connection element 7. Thus, it is possible to engage or disengage the supports 5, 6, as may be required under particular circumstances. It is thus also possible to easily remove the first and second supports by disengaging the connection.

The at least one connection element 7 may comprise a locking member for locking the first and second support members 5, 6, at a fixed angle relative to each other. This may thus enhance the pinching of the valve tissue, and further reduce the need for separate fastening elements 8. This also allows to provide a biased force directed towards the valve tissue by the first and second supports, which can be further enhanced by having angular portions 19, 19', 20, 20', towards the valve tissue as explained above.

In an example the first support member 5 and the second support member 6 comprises a depression at a centre region of the support members 5 and 6, at the periphery thereof. The depressions are opposite and aligned for forming a centre pivot point of the scissor linkage, i.e. the hinge. By having the first 5 and second 6 members comprising the depressions and which are opposite and aligned, the support members 5, 6 are in god contact with each other over a larger cooperating surface, giving a better and/or stronger pivot point than without any depressions and thus a better pinch effect.

In an example the first 5 and second 6 support members are arranged as the hinge in other locations than the centre region of the support members 5 and 6. In this way a less or greater pivot effect is achieved by the ends of the first 5 and second 6 support members. In an example the hinge is formed with a through hole on one support member and an extended pin or the like on the other support member so that they mate together and forms the hinge when arranged in contact with each other.

Figure 5:
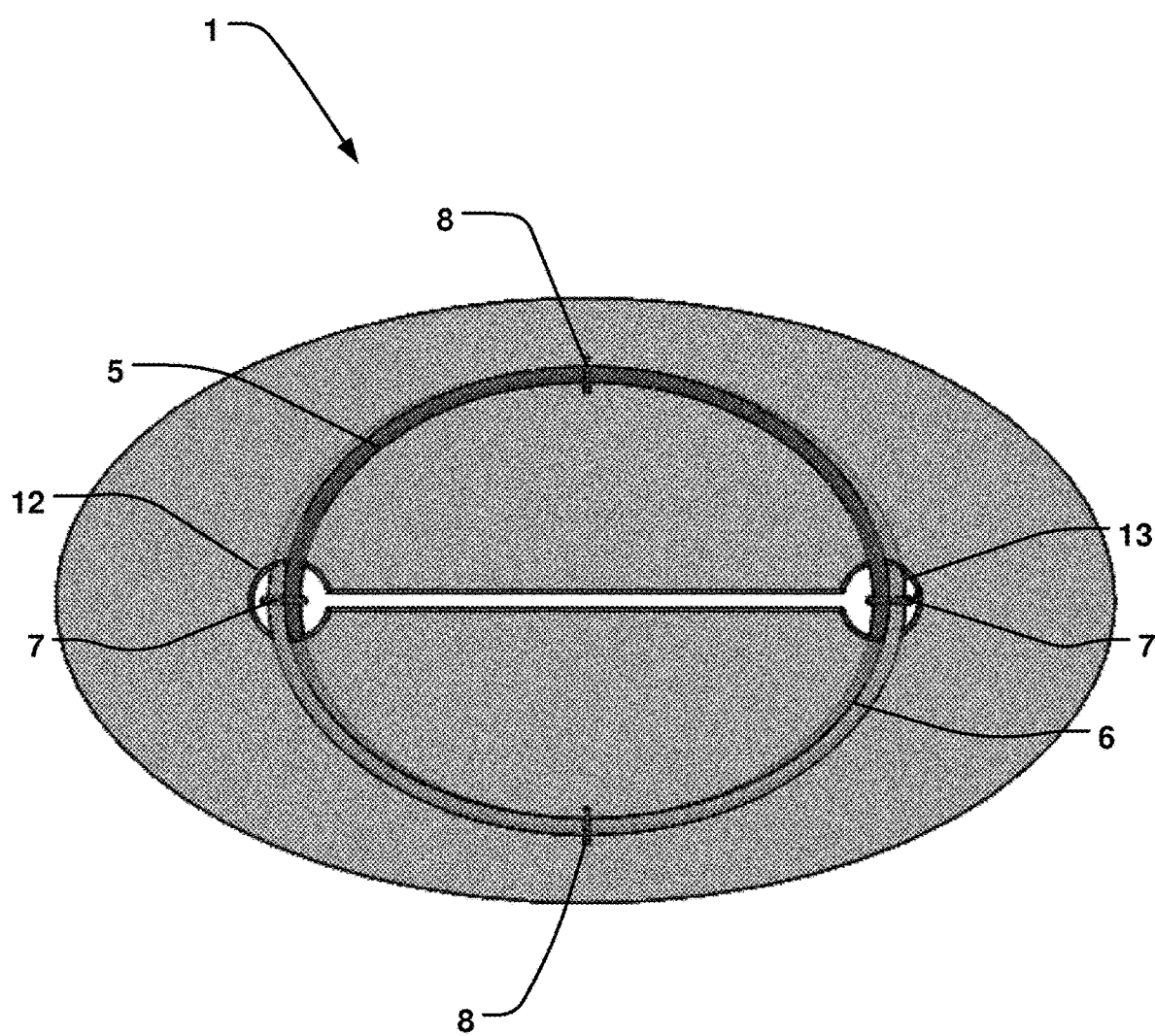
FIG. 5 is a top view of an annuloplasty device arranged in a heart according to an example of the invention.
Figure 6:
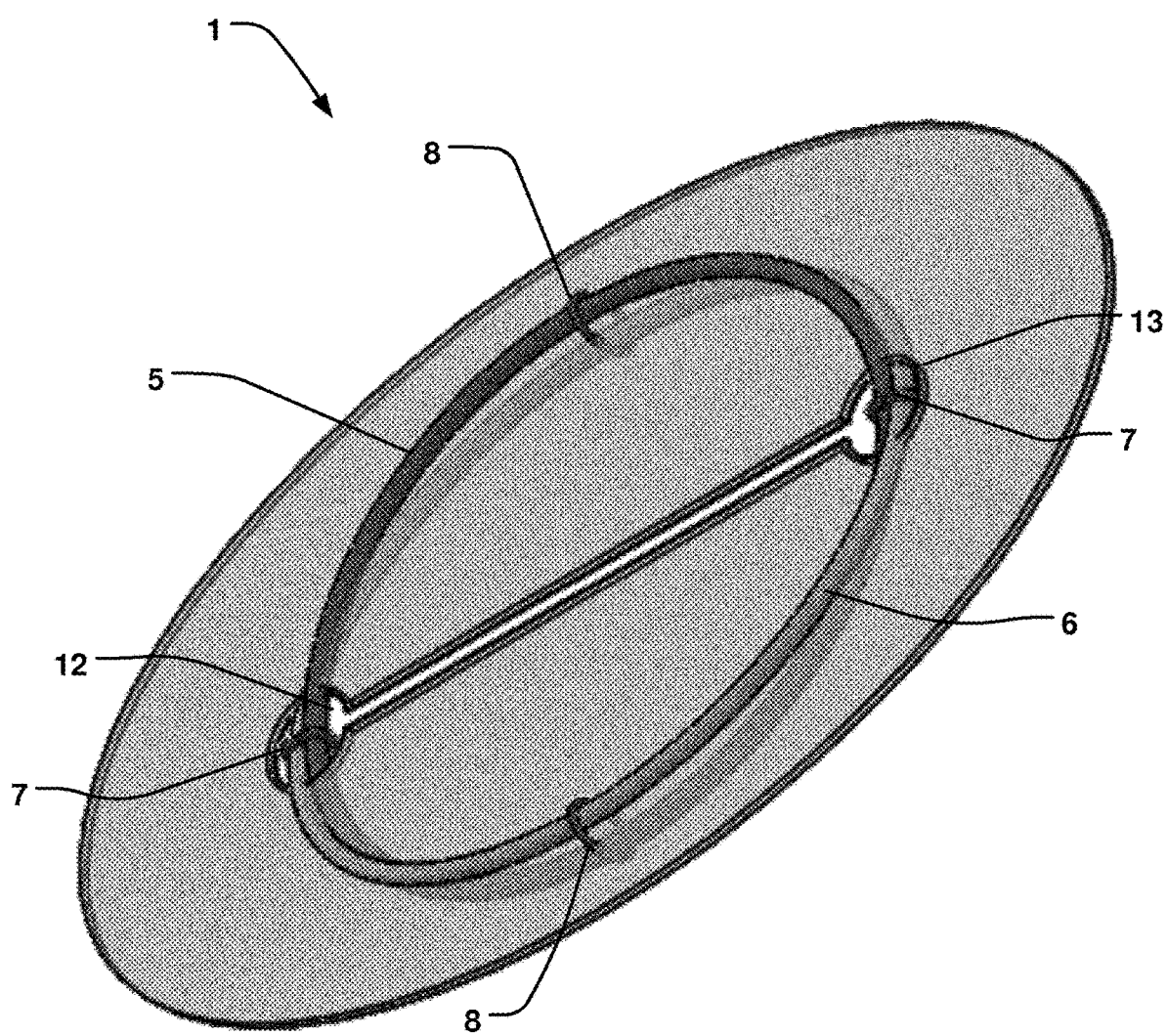
FIG. 6 is a side view of an annuloplasty device arranged in a heart according to an example of the invention.

In an example, illustrated in FIGS. 4, 5 and 6, connection element 7 and/or elements 7 are arranged around the first 5 and second 6 support members so as to hold the first 5 and second 6 support members together but still allow them to move, allowing the leaflets 15 to be pinched. In an example, the connection elements 7 may also be attached to the heart tissue at the commissures 12 and 13.

In another example the first support member 5 and the second support member 6 is of varying thickness. In one example the first support member 5 has one thickness that is different from the second 6 support member. In another example, the first 5 and/or second 6 support members have varying thickness along their respective lengths. In one example, the thickness is complementary matched between the first 5 and the second 6 support members so that an overall compact annuloplasty device 1 and/or a better grip between the two support members 5, 6 is achieved and/or better pinch effect of the leaflets 15. By having different thicknesses of the support members 5, 6 the device is customisable according to the patient's heart anatomy, defect of the heart, catheter and so on. The possibility to customise the device to the patient and/or delivery devices and/or defect is thus greatly improved. The first and second support members may thus also have tissue retention members (not shown) for anchoring against the annulus. This may aid in fixating the support members such as allowing tensioning the scissor linkage 18 at the commissures by rotation thereof to wedge the tissue at the commissures in the scissor linkage, and rotate the supports 5, 6, into the plane of the valve to clamp the tissue, whereby subsequent rotation in the counter direction is prevented due to the fixation of the support members with the tissue retention members. The tissue retention members may also have the function of a hook, which further reduce the need of having separate sutures, clips or fastening elements 8.

The placement of the annuloplasty device 1 at the desired location in the heart is performed in an example by entering the heart via a transcatheter approach, such as transapically or transfemorally, or through the atrium wall, or surgically through the atrium wall or via cannula. With catheter delivery, the first and second support members 5, 6, may be arranged so that they contact each other substantially along their circumference when being inserted into and through the catheter into the heart. In this way the first and second support members 5, 6 are moved apart from their holding and shaping surfaces which will contact the leaflets 15 but still arranged in such a way that they are loosely assembled and is easily manoeuvrable in the catheter and in the heart. This provides for an easy deployment and great manoeuvrability of the device 1.

In another example the first 5 and second 6 support members are delivered through the catheter separately and assembled overlapped together in the heart. The first support member 5 is first arranged at the leaflets 15 and the second support member 6 is arranged inside the first support member 5 so that they overlap and so that the second support member 6 is also in contact with the leaflets 15. In this way the first 5 and the second 6 support member both contact the leaflets 15 and forms the scissor linkage at the commissures so that they can pinch and reshape the heart valve.

Figure 7:
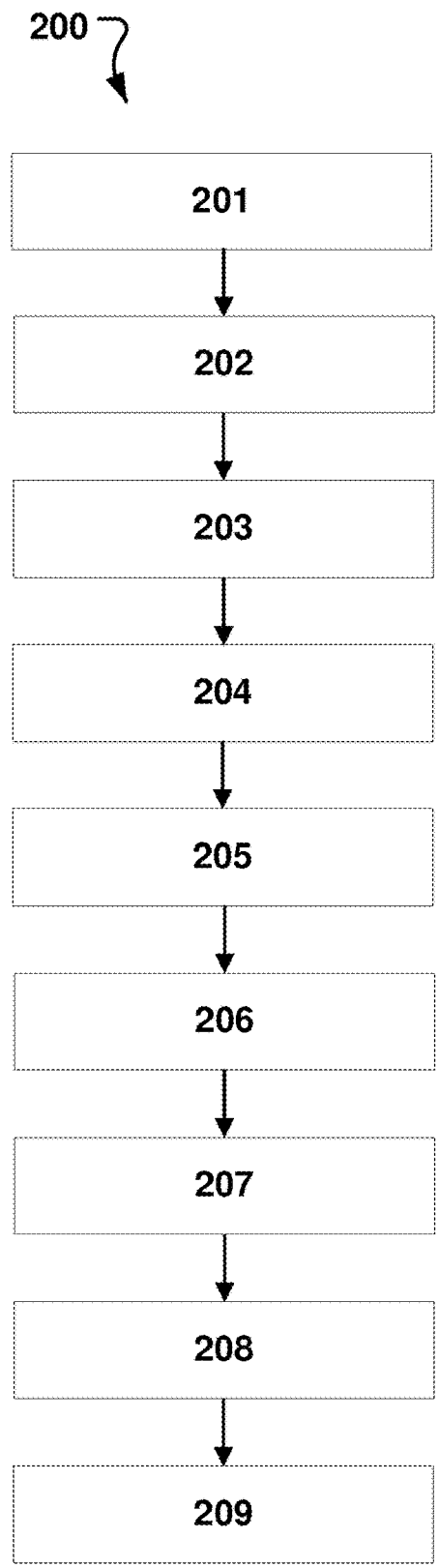
FIG. 7 is a flow chart illustrating a method according to an example of the invention.

FIG. 7 illustrates a method 200 of arranging an annuloplasty device comprising first 5 and a second 6 support members at a heart valve having leaflets and commissures, according to an example. The method 200 comprises; providing 201 access to the heart, arranging 202 the first support member to extend between the commissures and through the heart valve, whereby a proximal end of the first support member is configured to contact the atrial side of a first leaflet and a distal end is configured to abut a ventricular side of a second leaflet, arranging 203 the second support member to extend between the commissures and through the heart valve, whereby a proximal end of the first support member is configured to contact the atrial side of said second leaflet and a distal end is configured to abut a ventricular side of said second leaflet, and fixating 208 the first and second support members to pinch the tissue of said heart valve. This provides for the above mentioned beneficial effects as described with reference to FIGS. 1-6 for the annuloplasty device 1.

The fixating 208 may comprise attaching 209 said proximal end of said first support member to said distal end of said second support member to pinch the tissue therebetween at opposite sides of said heart valve. This is illustrated in FIG. 1b, where fastening element 8 secures the aforementioned proximal end of the first support member to the distal end of the second support member through the valve tissue.

In the method 200, the first and second support members may thus be overlapped 207 to form a scissor linkage 18 between said first and second support members at the commissures of said heart valve.

Further, as mentioned, the method 200 may comprise arranging 204 the first and second support members overlapped from the outside of the patient through a catheter and into the heart. Alternatively, the method 200 may comprise arranging 205 the first and second support members separately from the outside of the patient through a catheter and into the heart, and overlapping 206 the first and second support members at the heart valve.

The first 5 and second 6 support members are in an example attached to the leaflets 15 by a fastening element 8 and/or elements 8. The fastening elements 8 are arranged in an example at a 90 degree from the commissures, i.e. at a middle portion of the leaflet and/or annulus, as illustrated in FIGS. 5 and 6. The fastening elements 8 are in an example clips. The fastening elements 8 are in an example arranged to secure one of the support members at the leaflet or in another example both the support members at the same leaflet 15, as illustrated in FIG. 6. The scissor linkage allows for fixation of the annuloplasty device 1 with much fewer fastening elements 8. The angle formed between the overlapping first and second support members at the scissor linkage 18 prevents rotation of the support members 5,6, when positioned at opposite sides of the leaflets, since the commissures 12, 13, will be wedged in the scissor linkage 18, which is seen in FIG. 4. Thus fewer fastening element are required, which also is due to the pinching effect between the first and second support members, which is already obtained with a single fastening element 8 on each support 5, 6, as illustrated in FIG. 5.

The present disclosure has been described above with reference to specific examples. However, other examples than the above described are equally possible within the scope of the disclosure such as that more than two support elements can be used. Different method steps or a different order thereof than those described above may be provided within the scope of the disclosure. The different features and steps of the disclosure may be combined in other combinations than those described. The scope of the disclosure is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. An annuloplasty device configured to be implanted in a heart valve, said heart valve comprising valve tissue including an annulus and a pair of leaflets and having an atrial side and a ventricular side, said annuloplasty device comprising:
   a first support member and a second support member
   wherein the first and the second support members overlap and crisscross each other to form a scissor linkage and
   wherein the first and second support members are configured to pinch the leaflets.

2. The annuloplasty device according to claim 1, wherein the first and the second support members are formed as substantially elongated or substantially circular shaped continuous members and
   the continuous members comprise an opening for guiding around chordae, at an end of the first and second support members.

3. The annuloplasty device according to claim 1, wherein the first and the second support members are configured for encompassing substantially all chordae.

4. The annuloplast device according to claim 1, wherein the first support member and the second support member are parallel and arranged symmetrically relative to each other.

5. The annuloplasty device according to claim 1, wherein the first support member and the second support member are parallel and arranged asymmetrically relative to each other.

6. The annuloplasty device according to claim 1, wherein one or both of the first support member and the second support member are angulated.

7. The annuloplasty device according to claim 6, wherein one or both of the first support member and the second support member comprise angled portions at opposite ends thereof.

8. The annuloplasty device according to claim 1, wherein the scissor linkage comprises at least one connection element arranged at a periphery of said first and said second support members, whereby the first and the second support members are connected at said at least one connection element.

9. The annuloplasty device according to claim 8, wherein said connection element comprises a hinge or a pivot joint.

10. The annuloplasty device according to claim 8, wherein said first and said second support members are releasably connected at the at least one connection element.

11. The annuloplasty device according to claim 8, wherein said at least one connection element comprises a locking member that locks said first and said second support members at a fixed angle relative to each other.

12. The annuloplasty device according to claim 1, wherein the first support member and the second support member comprises a depression on a center region of the members, and wherein the depressions are opposite and aligned for forming a center pivot point of the scissor linkage.

13. The annuloplasty device according to claim 1, wherein the first support member and the second support member are of varying thickness.

14. The annuloplasty device according to claim 1, wherein the first support member entirely overlaps the second support member.

15. The annuloplasty device according to claim 1, wherein the first and the second support members are formed of a shape-memory material to have a relaxed, expanded shape and a compressed shape of reduced cross-section relative to the expanded shape.

16. An annuloplasty device configured to be implanted in a heart valve, said heart valve comprising valve tissue including an annulus and a pair of leaflets and having an atrial side and a ventricular side, said annuloplasty device comprising:
a first support member and a second support member that are rotatable relative to one another via a scissor linkage
wherein the first and the second support members overlap and crisscross each other and are configured such that rotation of the first and second support members relative to one another causes at least a portion of each of the first support member and the second support member to pinch the pair of leaflets from the ventricular side and the atrial side of the heart valve between said at least a portion of said first support member and said at least a portion of said second support member.

* * * * *